United States Patent [19]

Skipka et al.

[11] Patent Number: 4,496,764

[45] Date of Patent: Jan. 29, 1985

[54] PROCESS FOR THE PREPARATION OF 4-AMINO-3-METHYL-PHENOL

[75] Inventors: Guido Skipka, Bonn; Hans-Ulrich Alles; Gert Randau, both of Odenthal; Manfred Niese, Leverkusen, all of Fed. Rep. of Germany

[73] Assignee: Bayer Aktiengesellschaft, Leverkusen, Fed. Rep. of Germany

[21] Appl. No.: 457,834

[22] Filed: Jan. 14, 1983

Related U.S. Application Data

[63] Continuation of Ser. No. 275,538, Jun. 19, 1981, abandoned.

[30] Foreign Application Priority Data

Jul. 8, 1980 [DE] Fed. Rep. of Germany ....... 3025805

[51] Int. Cl.$^3$ ............................................. C07C 85/11
[52] U.S. Cl. .................................. 564/418; 564/422; 564/416
[58] Field of Search ........................ 564/418, 422, 416

[56] References Cited

U.S. PATENT DOCUMENTS

| | | | |
|---|---|---|---|
| 1,358,324 | 11/1920 | Moore | 564/418 X |
| 1,900,426 | 3/1933 | Busdorf et al. | 564/418 X |
| 1,921,120 | 8/1933 | Grether | 564/418 |
| 4,217,304 | 8/1980 | Albrecht et al. | 564/418 X |

FOREIGN PATENT DOCUMENTS

| | | | |
|---|---|---|---|
| 2534176 | 10/1977 | Fed. Rep. of Germany | 564/418 |
| 0155319 | 12/1920 | United Kingdom | 564/418 |

OTHER PUBLICATIONS

Augustine, "Catalytic Hydrogenation", p. 95 (1965).

*Primary Examiner*—Paul F. Shaver
*Attorney, Agent, or Firm*—Sprung, Horn, Kramer & Woods

[57] ABSTRACT

A process for the preparation of 4-amino-3-methyl-phenol from 4-nitroso-3-methyl-phenol, which comprises contacting said 4-nitroso-3-methyl-phenol with iron in an acid aqueous medium at a temperature of 20° to 100° C. said medium having pH in the range from 2 to 6.5.

15 Claims, No Drawings

PROCESS FOR THE PREPARATION OF 4-AMINO-3-METHYL-PHENOL

This is a continuation of application Ser. No. 275,538, filed June 19, 1981, abandoned.

The invention relates to a process for the preparation of 4-amino-3-methyl-phenol from 4-nitroso-3-methyl-phenol.

It is known to dissolve 4-nitroso-3-methyl-phenol in aqueous ammonia and to reduce it to 4-amino-3-methyl-phenol with hydrogen sulphide (J. org. Chem. 12, 417 (1947)).

The disadvantage of this process is that it is carried out in the presence of hydrogen sulphide, since, because of the toxicity of the hydrogen sulphide, expensive safety measures must be taken and this adversely affects the economics of the process.

A process has now been found for the preparation of 4-amino-3-methyl-phenol from 4-nitroso-3-methyl-phenol, which is characterised in that 4-nitroso-3-methyl-phenol is reacted with iron in an acid aqueous medium at temperatures from 20° to 100° C. and in a pH range from 2 to 6.5.

The reaction according to the invention is in general carried out with 1.2 to 10 times the equivalent amount of iron, preferably with 2 to 4 times the equivalent amount of iron.

The iron is in general employed in the process according to the invention in the form of iron turnings. It is possible to use iron turnings of various qualities and particle sizes. Sieved iron turnings with a low dust content are preferably used.

The iron is usually added to the reaction mixture all at once, before the start of the reaction.

The process according to the invention is in general carried out at temperatures from 20° to 100° C., preferably at 30° to 50° C.

The process according to the invention is usually carried out in a pH range from 2 to 6.5, preferably in a range from 5 to 6 and particularly preferably in a pH range from 5.2 to 5.9.

Various inorganic or organic acids, such as hydrochloric acid, sulphuric acid or aliphatic carboxylic acids with 2 to 7 carbon atoms, preferably 2 to 5 carbon atoms, can be employed for the preparation of the aqueous acid medium in which the reaction according to the invention is carried out. Examples of aliphatic carboxylic acids which are mentioned are: acetic acid, propionic acid and butyric acid. Acetic acid is preferably employed in the process according to the invention.

The process according to the invention is in general carried out by a procedure in which the iron turnings are initially introduced into the reaction vessel in a mixture of water and the appropriate acid, this suspension is warmed to the appropriate reaction temperature and the 4-nitroso-3-methyl-phenol is then added, as a suspension in water, to the acid iron turnings suspension.

It is also possible to add the 4-nitroso-3-methyl-phenol to the acid iron turnings suspension in the form of a solid.

The mixture of water and 4-amino-3-methyl-phenol which contains iron oxide and is obtained after the reaction is separated off from the excess iron, after adding sodium sulphite and 50% strength sodium hydroxide solution to the reaction mixture, and, after separating off the iron oxide, is processed further. The residual iron which has not been consumed is replenished by the amount of iron which has reacted, and is used again for a further reduction.

The process according to the invention is in general carried out under normal pressure. However, it is also possible to carry out the process under reduced or increased pressure.

The process according to the invention can be carried out either discontinuously or continuously.

The advantages of the process according to the invention are the simple reaction procedure, together with a high yield and good quality of 4-amino-3-methyl-phenol.

It is surprising that the process according to the invention proceeds so selectively, that is to say without the formation of undesired by-products and condensation products.

4-Amino-3-methyl-phenol is used as an intermediate product for the preparation of plant protection agents (compare German Auslegeschrift No. 1,145,162; and CA 59, 9885$^d$ (1963)).

EXAMPLE 600 g of iron turnings, 500 ml of water and 1 ml of acetic acid were initially introduced into a glass apparatus consisting of a 3 l five-necked sulphonation beaker into which a bar-type stirrer of stainless steel, an internal thermometer and a dropping funnel with a stirrer are inserted, the mixture being warmed to a temperatue of 35° C.

196.5 g of 4-nitroso-3-methyl-phenol (75.8% pure material, corresponding to 1.087 mols) were suspended in 300 ml of water. The suspension was introduced into the acid iron turnings suspension in the course of 40 minutes. During the introduction of the suspension, the outflow of a sample on blotting paper after spotting with 1N sodium hydroxide solution had to remain light-coloured. A further 4 ml of acetic acid were added in the course of the reduction. The temperature during the reduction was kept at 40° C. with 800 g of ice. Reduction was continued for a further 30 minutes, 25 g of sodium sulphite were then added to the batch and the batch was warmed to 80° C. After this temperature had been reached, the reaction mixture was adjusted to a pH value of 12 with 85 ml of 50% strength sodium hydroxide solution and the suspension was immediately sucked through a filter onto 310 ml of crude hydrochloric acid. The iron oxide residue was washed with a little hot water. 35 g of active charcoal were added to the clear solution and the mixture was filtered at a temperature of 90° C. With the aid of diazotization, 1.069 mols of product were found in 2,300 ml of filtrate, which corresponds to a yield of 98.3% of theory.

What is claimed is:

1. A process for the preparation of 4-amino-3-methyl-phenol from 4-nitroso-3-methyl-phenol, which comprises contacting said 4-nitroso-3-methyl-phenol with iron in an acid aqueous medium at a temperature of 20° to 100° C. said medium having a pH in the range from 2 to 6.5.

2. A process according to claim 1, wherein the reaction is carried out at a temperature from 30° to 50° C.

3. A process according to claim 1, wherein the reaction is carried out at a pH in the range from 5 to 6.

4. A process according to claim 1, wherein the reaction is carried out at a pH from 5.2 to 5.9.

5. A process according to claim 1, wherein the reaction is carried out with 1.2 to 10 times the equivalent amount of iron.

6. A process according to claim 1, wherein the reaction is carried out with 2 to 4 times the equivalent amount of iron.

7. A process according to claim 1, wherein the acid of said acid aqueous medium in an inorganic or organic acid.

8. A process according to claim 7, wherein said acid is an inorganic acid.

9. A process according to claim 8, wherein said inorganic acid is hydrochloric acid or sulfuric acid.

10. A process according to claim 9, wherein said acid is hydrochloric acid.

11. A process according to claim 1, wherein the said acid is an aliphatic carboxylic acid of 2 to 7 carbon atoms.

12. A process according to claim 11, wherein said aliphatic carboxylic acid has between 2 and 5 carbon atoms.

13. A process according to claim 12, wherein said aliphatic carboxylic acid is selected from the group consisting of acetic acid, propionic acid and butyric acid.

14. A process according to claim 13, wherein said acid is acetic acid.

15. A process according to claim 1, wherein said iron is in the form of iron turnings.

* * * * *